(12) United States Patent
Ahmann et al.

(10) Patent No.: US 9,113,956 B2
(45) Date of Patent: Aug. 25, 2015

(54) ISOMARK TATTOOING DEVICES

(75) Inventors: Robert D. Ahmann, Rochester, MN (US); James A. Starr, Soquel, CA (US); Broc T. Giffey, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 400 days.

(21) Appl. No.: 13/404,622

(22) Filed: Feb. 24, 2012

(65) Prior Publication Data

US 2012/0221036 A1 Aug. 30, 2012

Related U.S. Application Data

(60) Provisional application No. 61/463,986, filed on Feb. 25, 2011.

(51) Int. Cl.
*A01K 11/00* (2006.01)
*A61B 19/00* (2006.01)
*A61M 37/00* (2006.01)

(52) U.S. Cl.
CPC ............ *A61B 19/54* (2013.01); *A01K 11/005* (2013.01); *A61M 37/0076* (2013.01); *A61B 2019/545* (2013.01)

(58) Field of Classification Search
CPC . A01K 11/00; A01K 11/005; A61M 37/0076; A61M 37/0084
USPC .............. 128/897, 898; 606/1, 116, 117, 166, 606/181, 182, 185, 186; 600/426
See application file for complete search history.

(56) References Cited

U.S. PATENT DOCUMENTS

| | | | |
|---|---|---|---|
| 1,489,558 A * | 4/1924 | Timson | 606/116 |
| 1,699,012 A | 1/1929 | Naylor | |
| 3,039,467 A * | 6/1962 | Stone et al. | 606/116 |
| 4,279,259 A * | 7/1981 | Lee et al. | 600/587 |
| 4,392,493 A * | 7/1983 | Niemeijer | 606/116 |
| 4,437,361 A * | 3/1984 | Steckel et al. | 81/9.22 |
| 4,440,168 A * | 4/1984 | Warren | 606/102 |
| 4,508,106 A * | 4/1985 | Angres | 128/898 |
| 4,608,045 A * | 8/1986 | Fretwell | 604/311 |
| 4,665,912 A * | 5/1987 | Burton | 606/185 |
| 4,914,988 A * | 4/1990 | Chang | 81/9.22 |
| 5,026,388 A | 6/1991 | Ingalz | |

(Continued)

FOREIGN PATENT DOCUMENTS

WO WO 2010091137 A2 * 8/2010

OTHER PUBLICATIONS

International Search Report and Written Opinion issued in PCT/US2010/023313, mailed Sep. 14, 2010, 8 pages.

(Continued)

*Primary Examiner* — Ryan Severson
(74) *Attorney, Agent, or Firm* — Faegre Baker Daniels LLP

(57) ABSTRACT

A device and method for marking a treatment isocenter on a patient's body. One embodiment includes a base including alignment indicia, a marker disposed over the base and positioned relative to the indicia for marking the isocenter on the patient's body and an actuator for actuating the marker and causing a mark indicating the isocenter to be made on the patient's body. The actuator can include a button and a spring coupled to the marker. Compressing the actuator causes the marker to travel through an ink well prior to piercing the patient's skin.

22 Claims, 20 Drawing Sheets

(56) References Cited

U.S. PATENT DOCUMENTS

| | | | |
|---|---|---|---|
| 5,231,993 A | 8/1993 | Haber et al. | |
| 5,306,271 A * | 4/1994 | Zinreich et al. | 606/1 |
| 5,368,030 A * | 11/1994 | Zinreich et al. | 600/414 |
| 5,407,440 A * | 4/1995 | Zinreich et al. | 606/1 |
| 5,469,847 A * | 11/1995 | Zinreich et al. | 600/414 |
| 5,496,304 A | 3/1996 | Chasan | |
| 5,569,237 A * | 10/1996 | Beckenstein | 606/1 |
| 5,643,306 A | 7/1997 | Schraga | |
| 5,680,872 A | 10/1997 | Sesekura et al. | |
| 5,690,107 A | 11/1997 | Hofmann | |
| 5,713,890 A * | 2/1998 | Chasan | 606/1 |
| 5,743,899 A | 4/1998 | Zinreich | |
| 5,833,649 A * | 11/1998 | Atef | 604/500 |
| 5,988,174 A * | 11/1999 | Chasan | 128/898 |
| 5,997,501 A | 12/1999 | Gross et al. | |
| 6,056,737 A | 5/2000 | Rosen | |
| 6,197,034 B1 * | 3/2001 | Gvozdic et al. | 606/116 |
| 6,540,756 B1 * | 4/2003 | Vaughan | 606/116 |
| 6,588,301 B1 * | 7/2003 | Chanet et al. | 81/9.22 |
| 6,612,262 B2 * | 9/2003 | Julien et al. | 119/712 |
| 6,901,885 B1 * | 6/2005 | Kleinsasser | 119/842 |
| 6,923,816 B1 | 8/2005 | Passmore | |
| 7,166,852 B2 | 1/2007 | Saracen et al. | |
| 7,494,493 B2 * | 2/2009 | Matsuura | 606/116 |
| 8,480,684 B2 | 7/2013 | Bendre et al. | |
| 2003/0187458 A1 * | 10/2003 | Carlson, II | 606/116 |
| 2003/0195523 A1 * | 10/2003 | Futsz | 606/117 |
| 2004/0267283 A1 | 12/2004 | Mavor et al. | |
| 2005/0245948 A1 | 11/2005 | Khalaj | |
| 2005/0277973 A1 * | 12/2005 | Huang et al. | 606/185 |
| 2006/0079910 A1 * | 4/2006 | Tartaglia | 606/116 |
| 2007/0203504 A1 * | 8/2007 | Denny et al. | 606/116 |
| 2008/0208236 A1 * | 8/2008 | Hobbs et al. | 606/186 |
| 2008/0269687 A1 | 10/2008 | Chong et al. | |
| 2008/0287782 A1 | 11/2008 | Traboulsi et al. | |
| 2008/0287978 A1 | 11/2008 | Hickman, III | |
| 2010/0004532 A1 | 1/2010 | Bendre et al. | |
| 2010/0137710 A1 * | 6/2010 | Zavislan et al. | 600/426 |
| 2012/0029548 A1 | 2/2012 | Giffey | |
| 2012/0221036 A1 * | 8/2012 | Ahmann et al. | 606/186 |
| 2014/0107662 A1 * | 4/2014 | Goolishian | 606/117 |

OTHER PUBLICATIONS

Definition of Indicia, downloaded from http://dictionary.reference.com/browse/indicia?s=t on Nov. 18, 2013, 1 page.

* cited by examiner

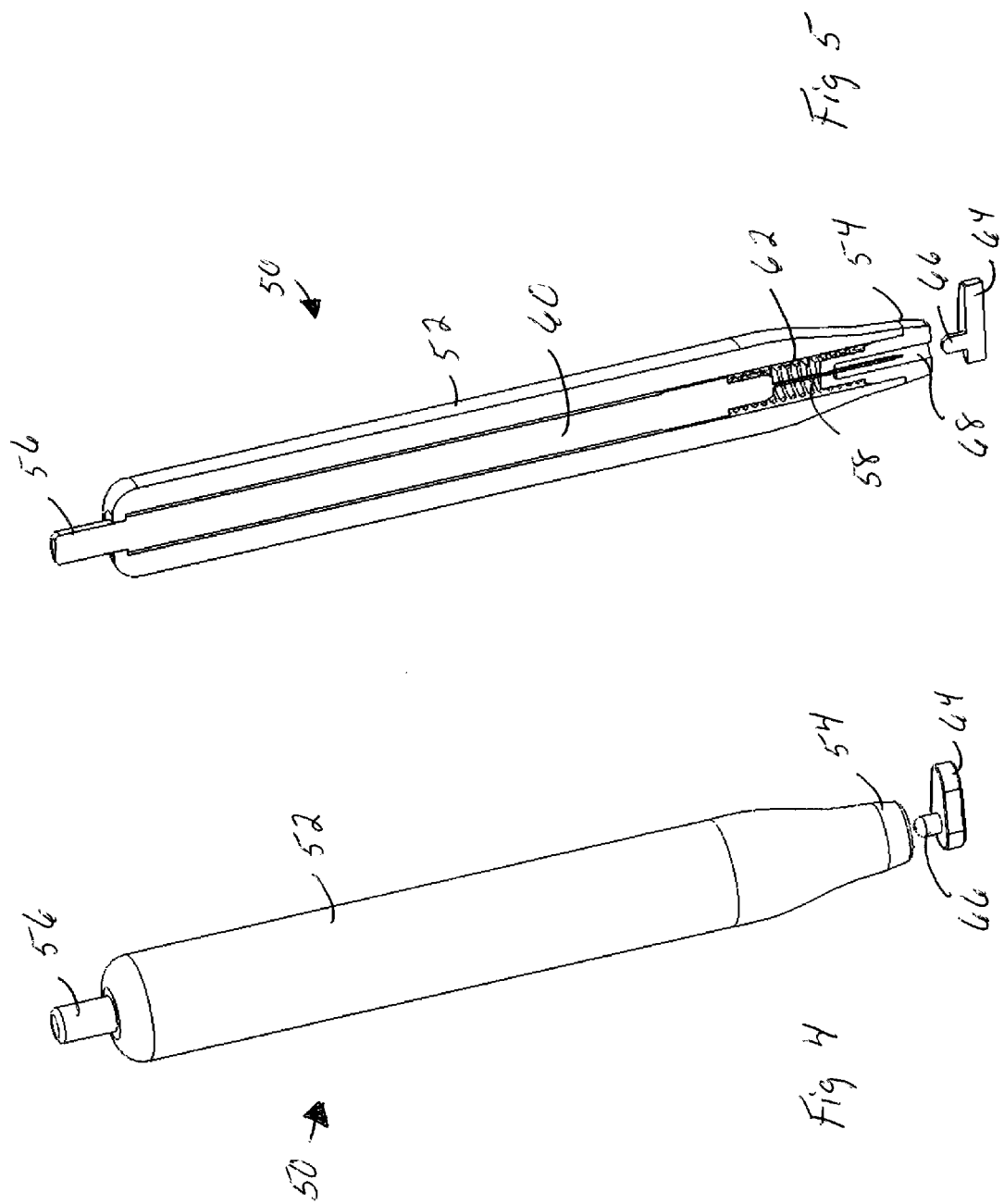

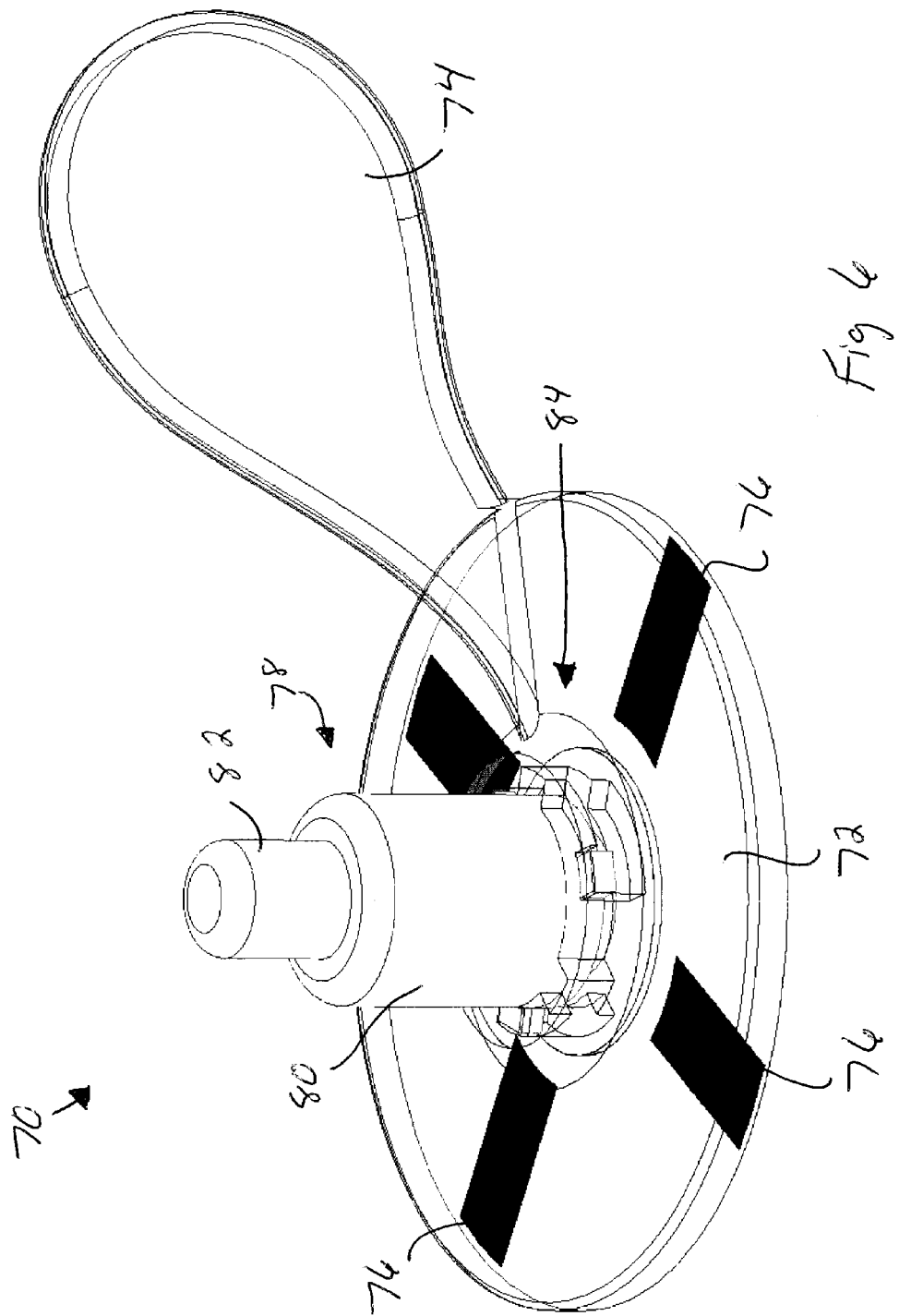

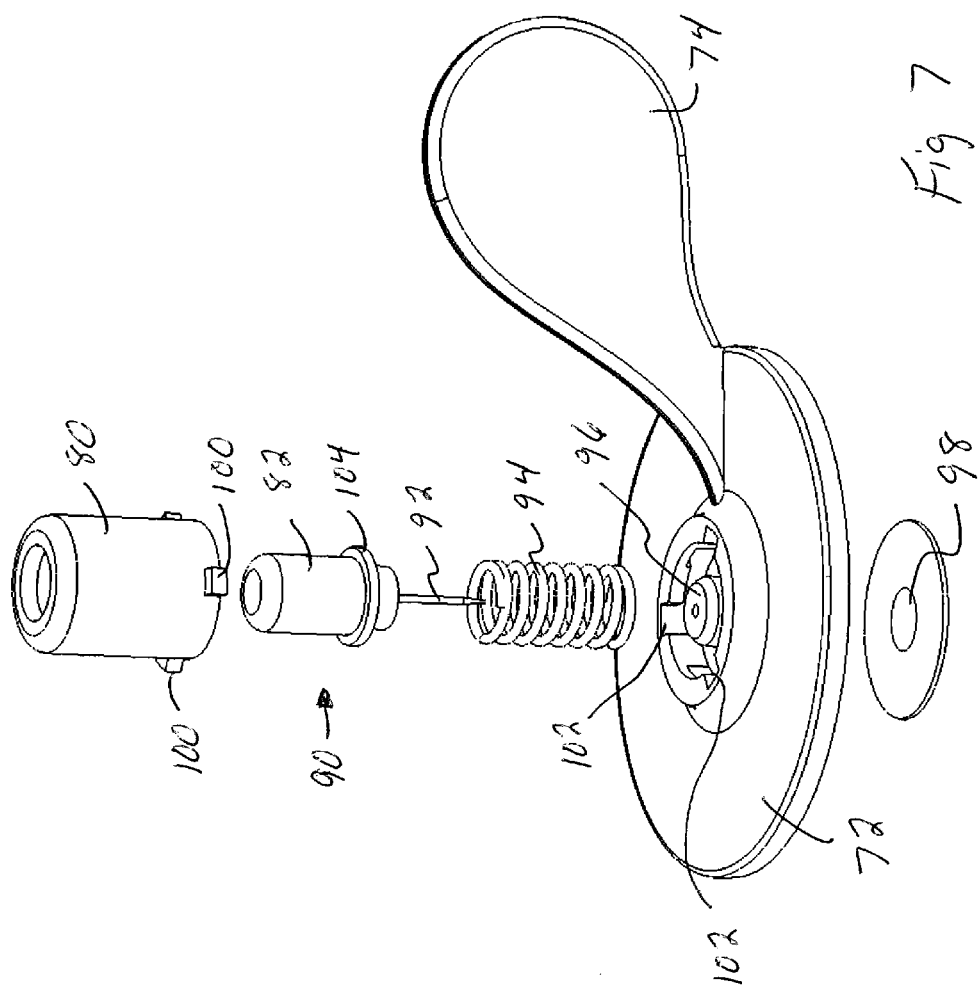

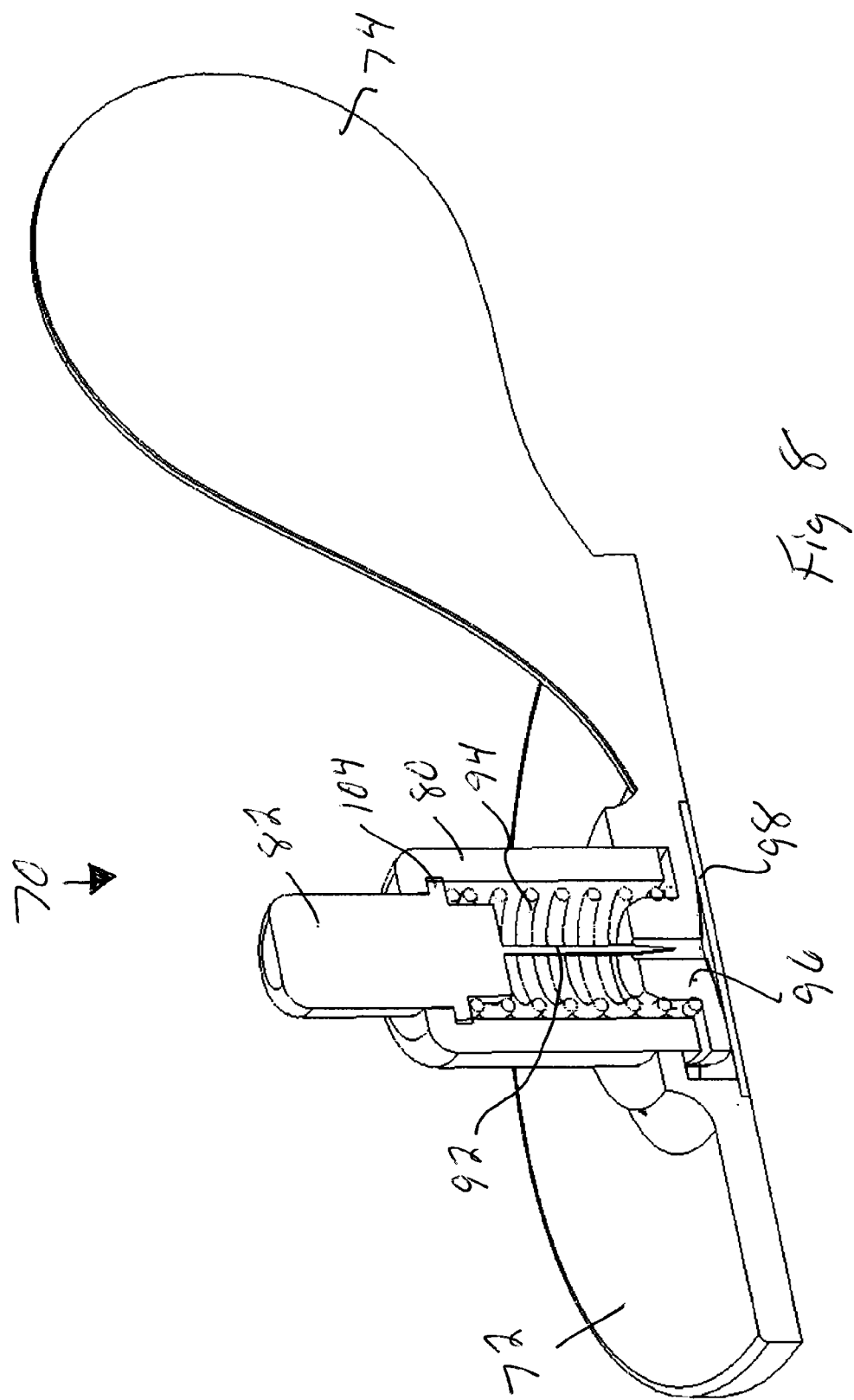

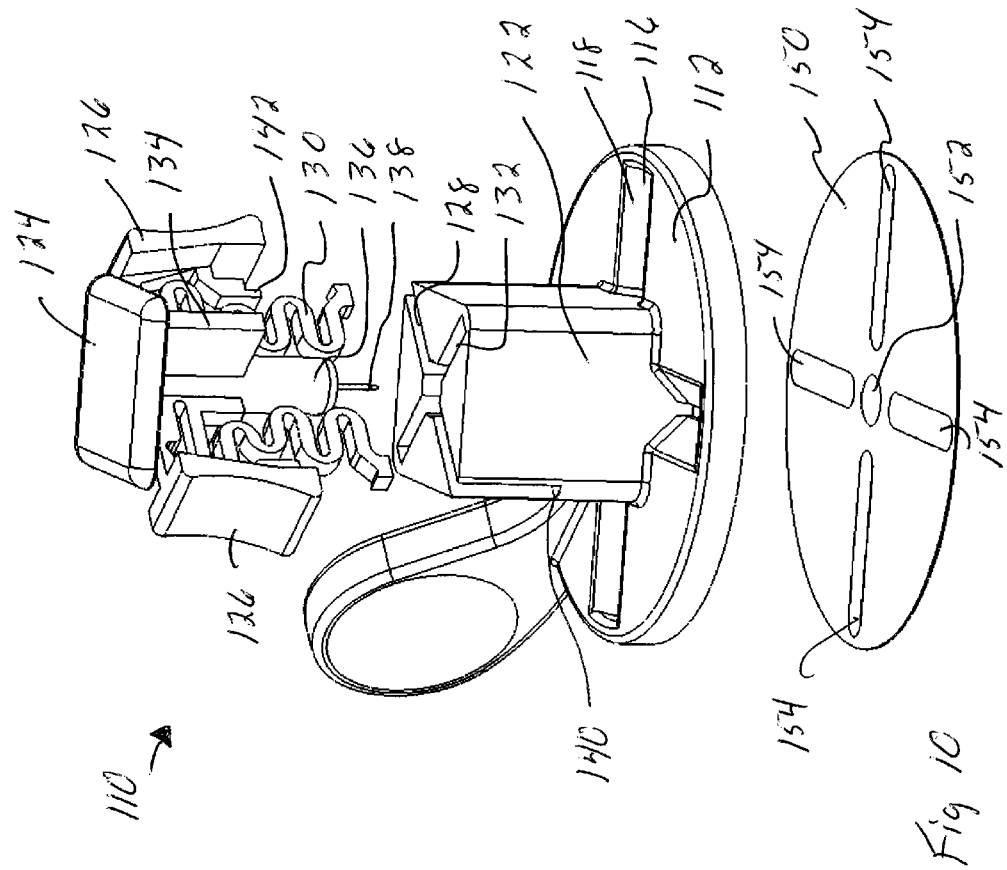

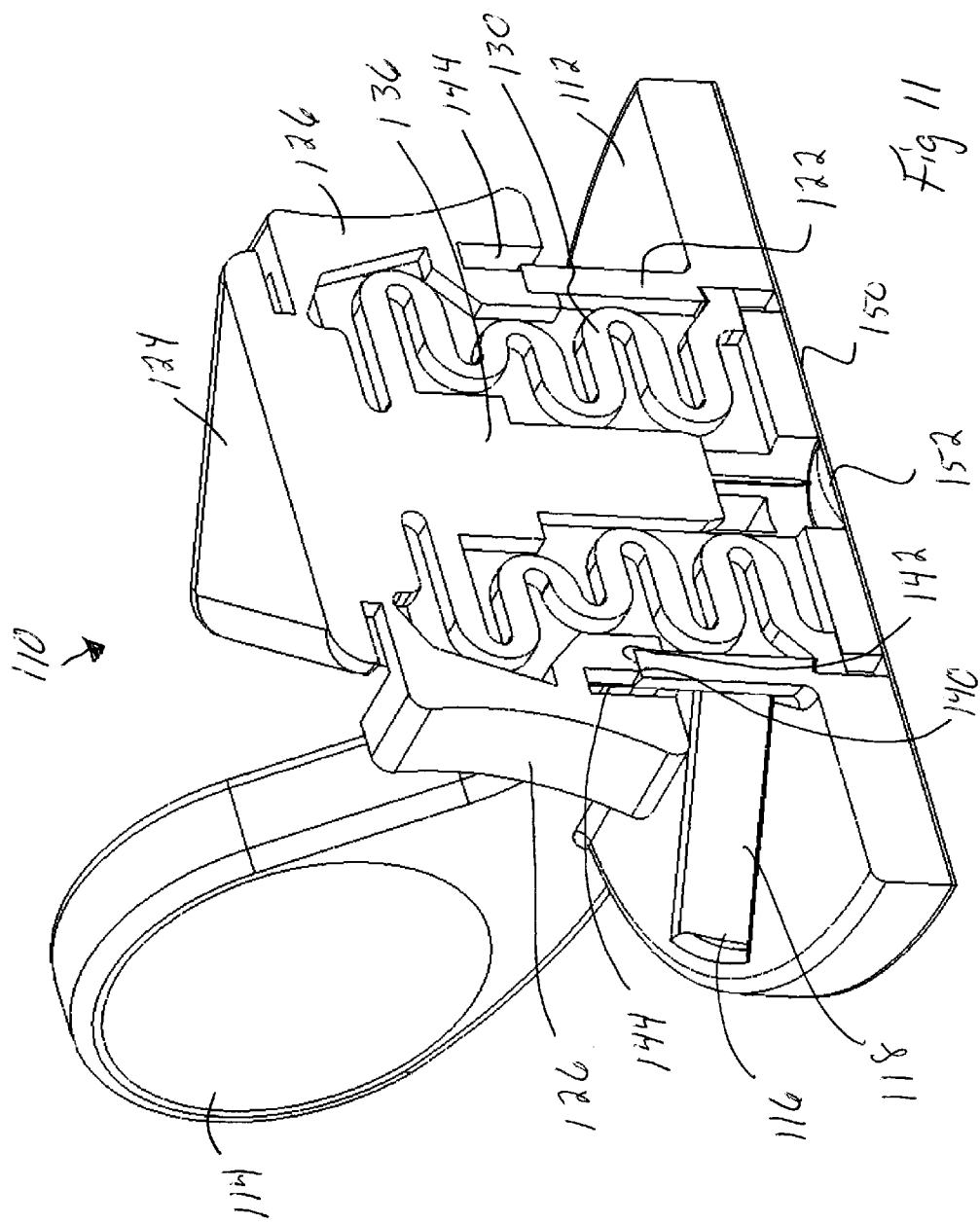

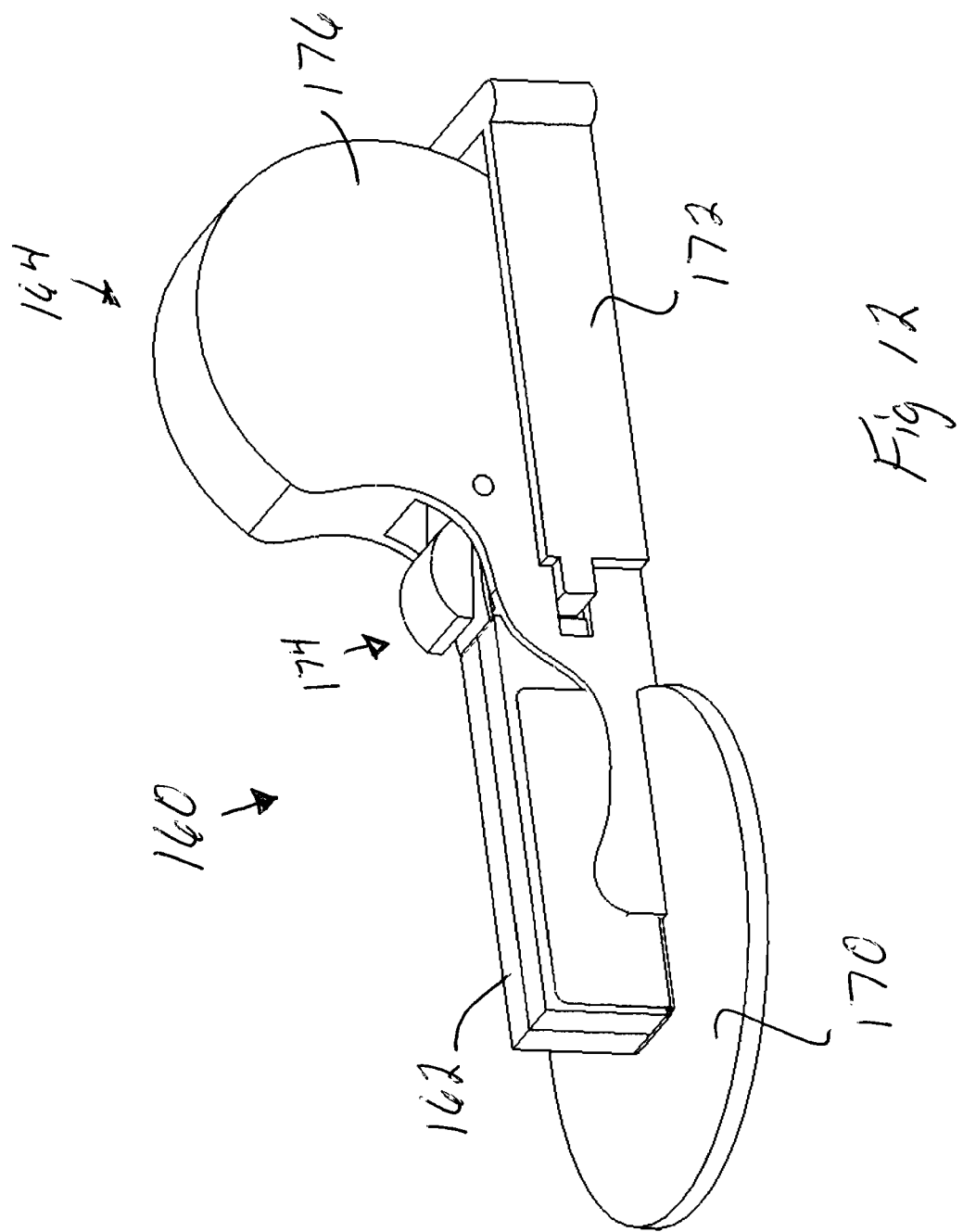

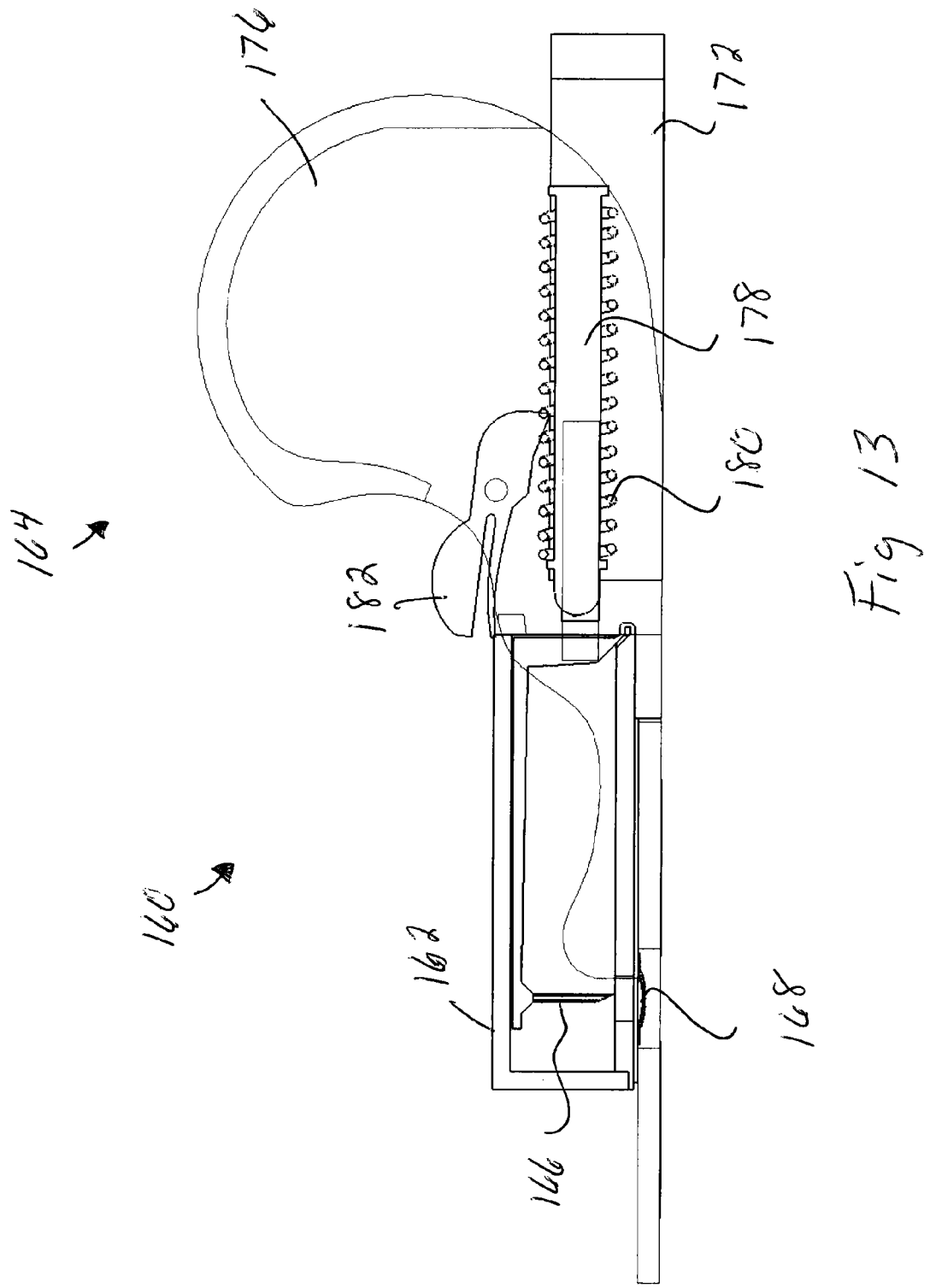

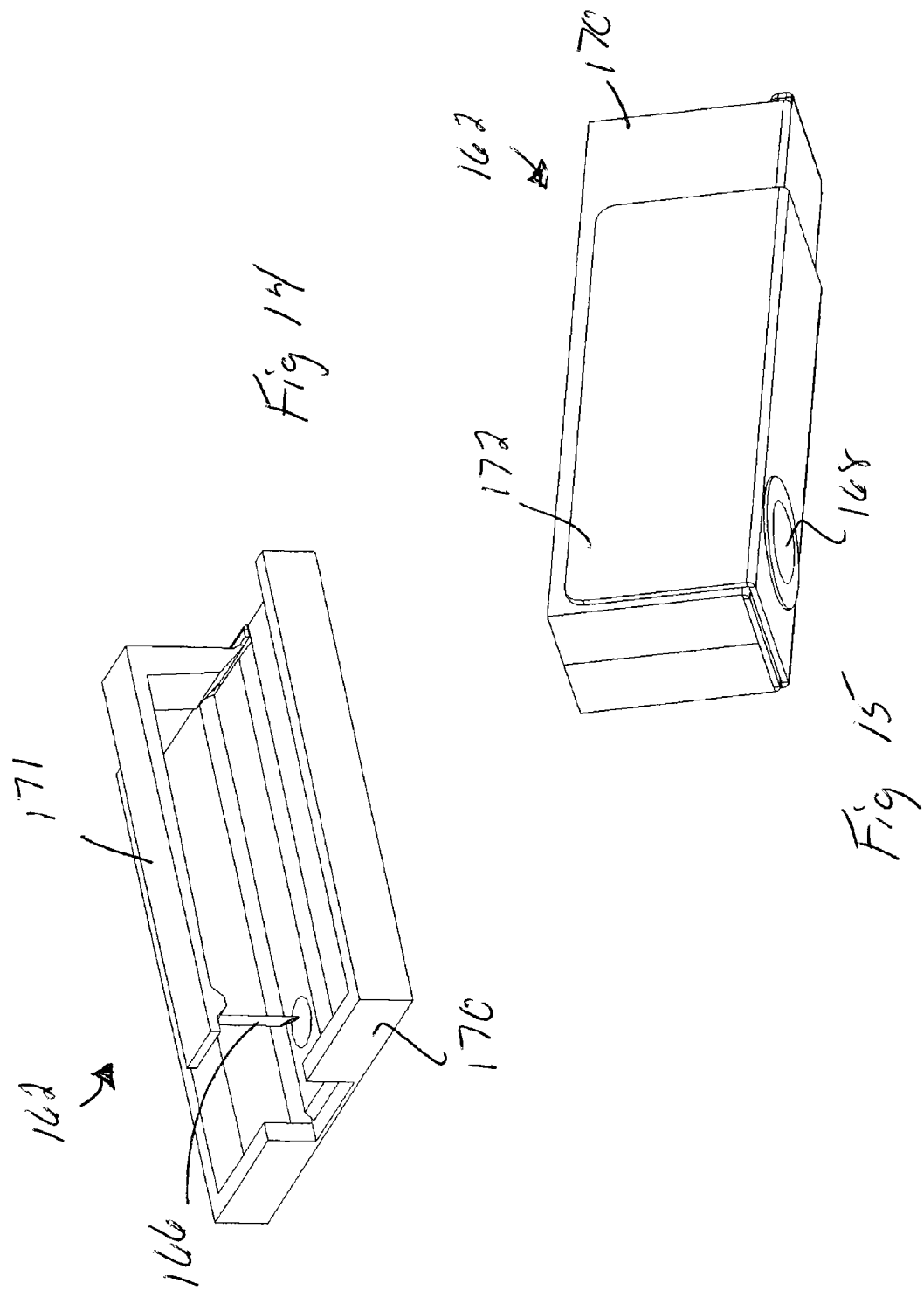

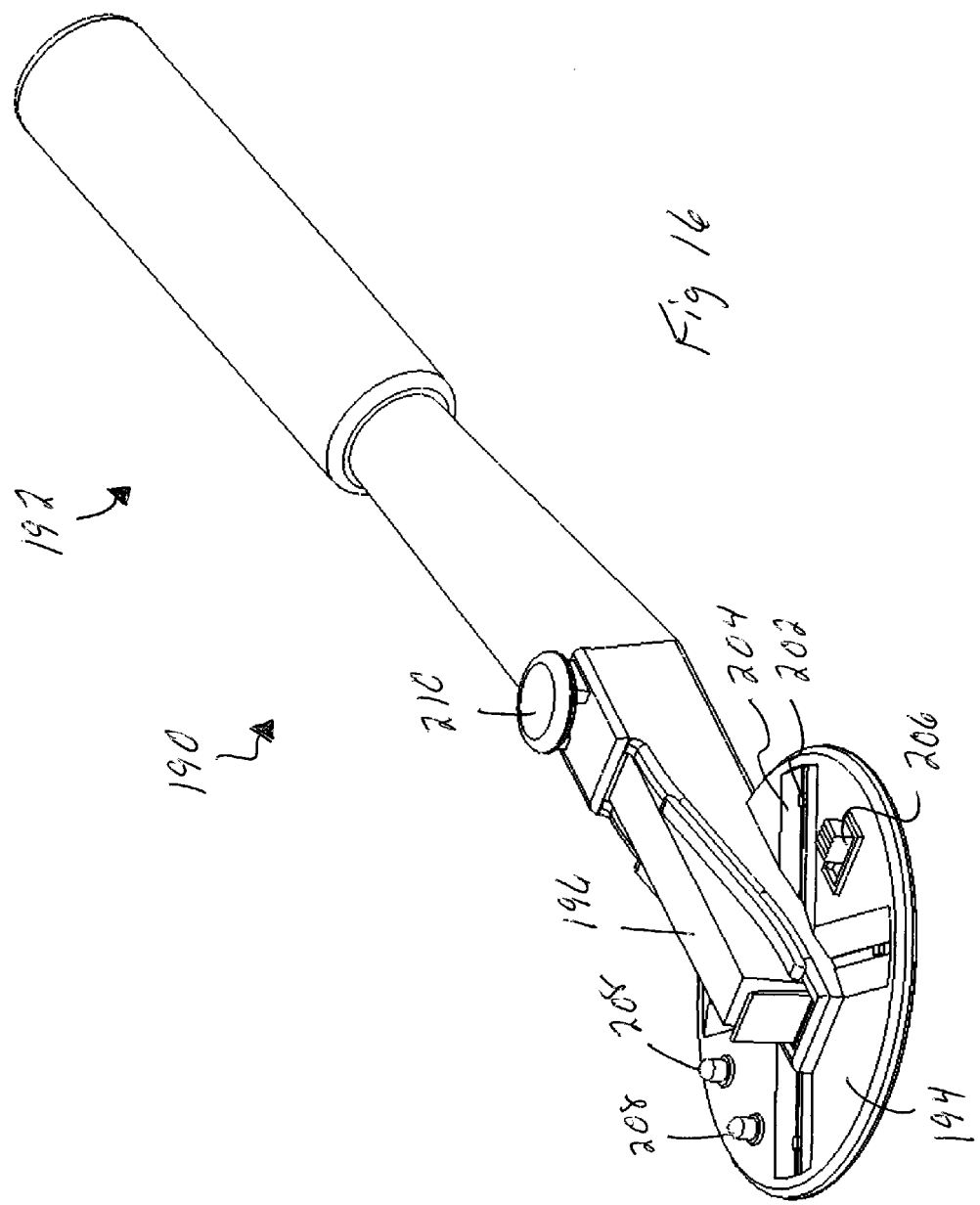

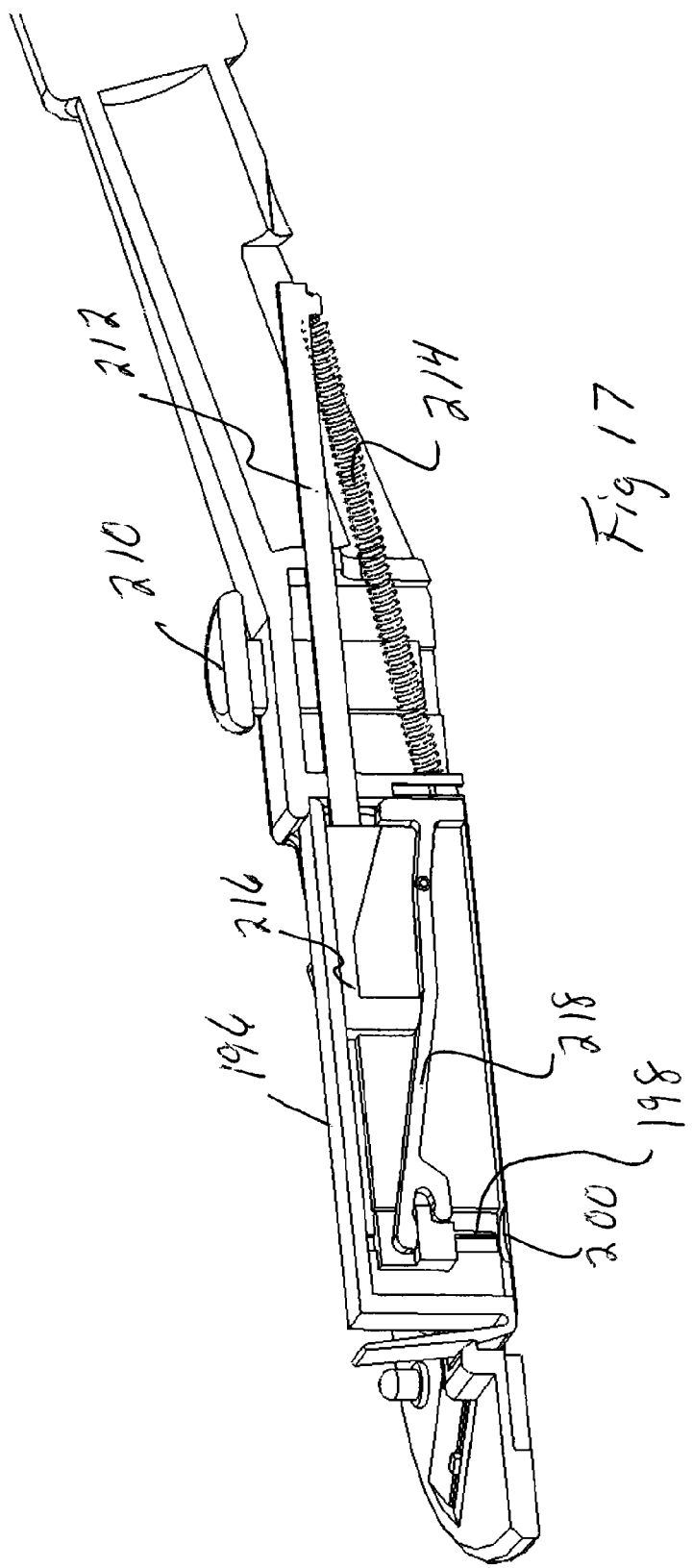

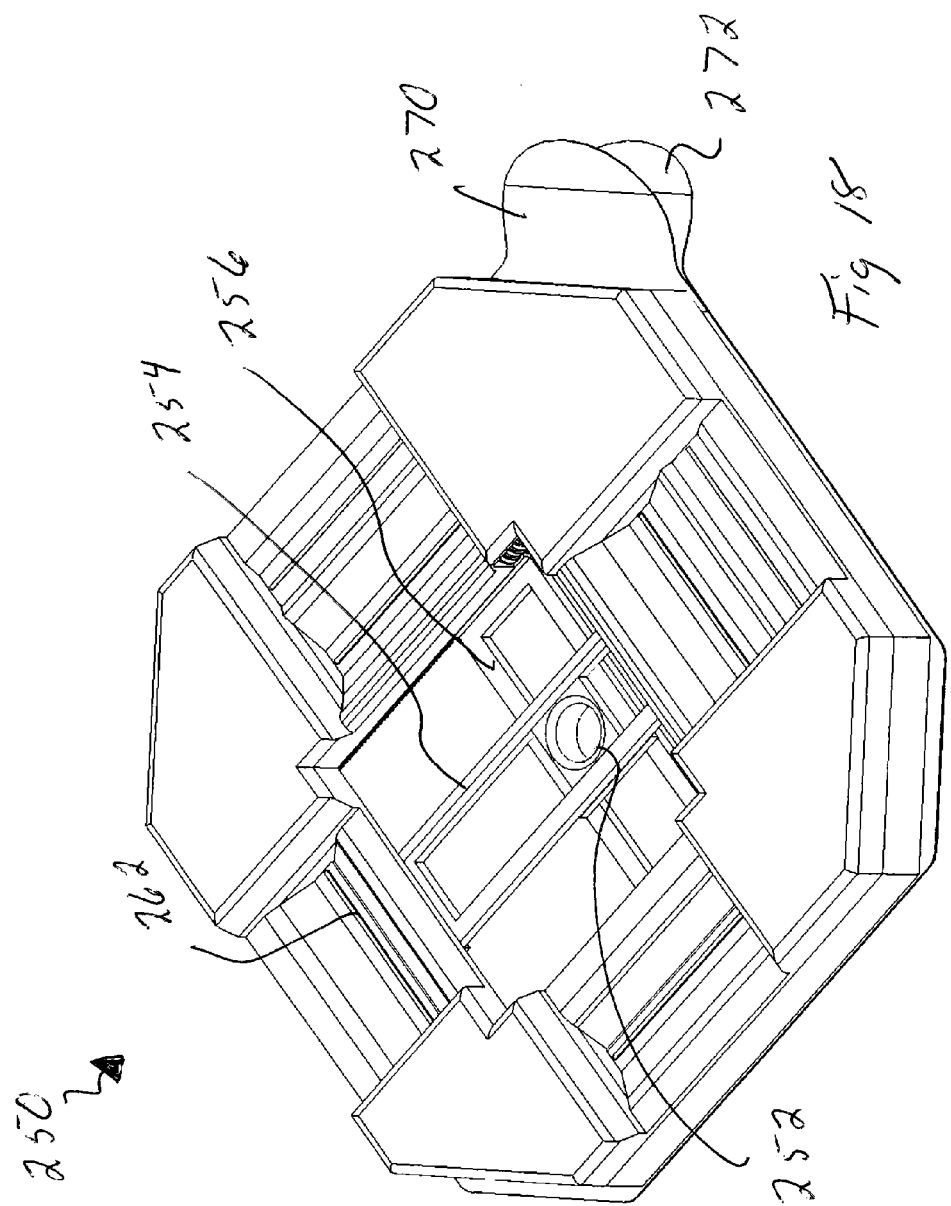

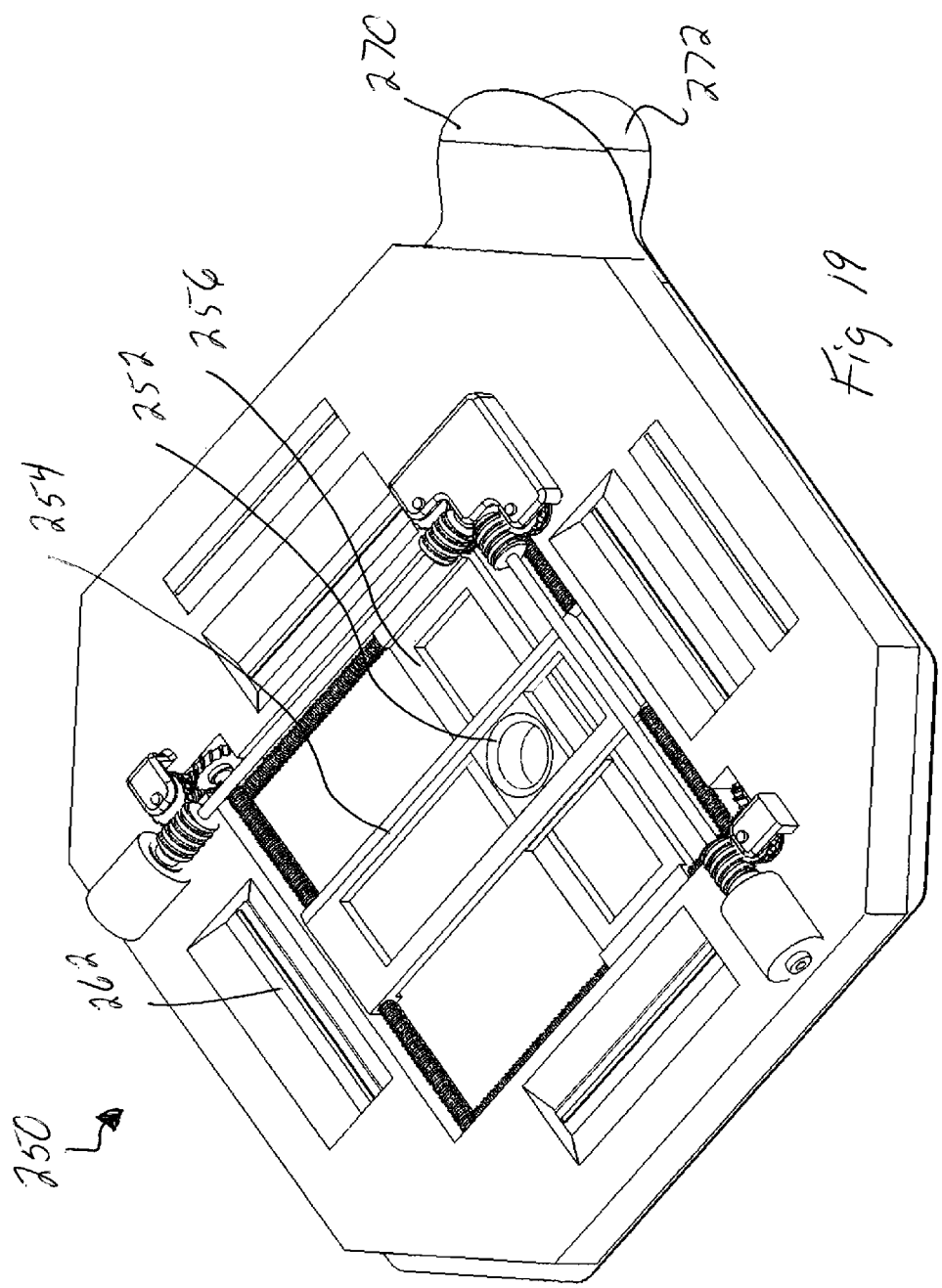

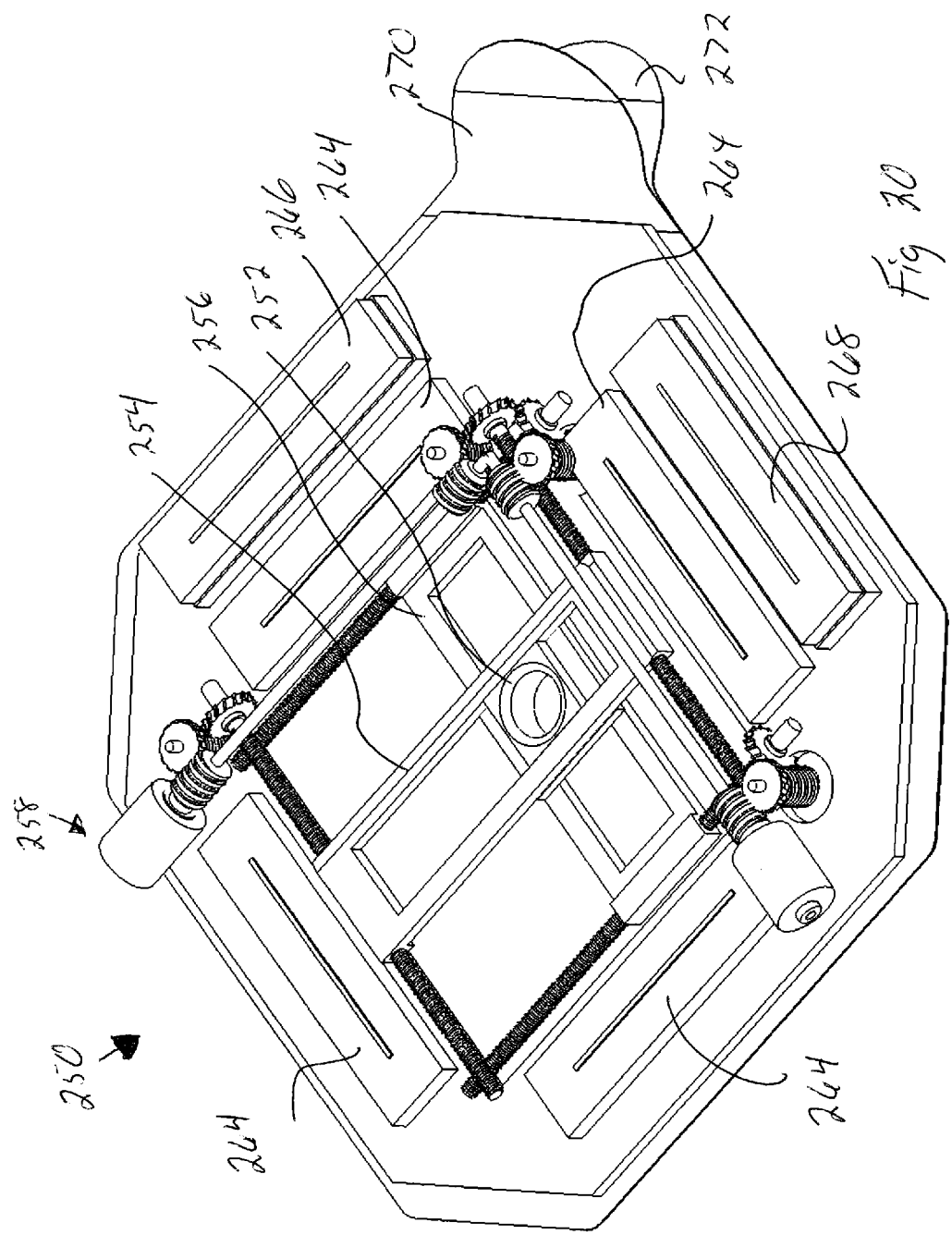

ISOMARK TATTOOING DEVICES

CROSS-REFERENCE TO RELATED APPLICATION

This application claims the benefit of U.S. provisional application no. 61/463,986 filed Feb. 25, 2011, entitled IMPROVED ISOMARK TATTOOING DEVICE EMBODIMENTS, the disclosure of which is hereby incorporated by reference in its entirety for all purposes.

TECHNICAL FIELD

The present invention relates to a marking device. More particularly, the present invention relates to a device and a method for marking a treatment isocenter on a patient's body.

BACKGROUND

Before receiving radiation therapy treatment, a computed axial tomography simulation (CAT scan or CT scan) is typically performed. A CT scan is used to help the radiation oncologist map the target treatment area on a patient's body. Dosimetrists and physicists plan the treatment from the CT images. The CT scan is performed with the patient in a comfortable, yet stable position for the area being treated. With the patient in the desired treatment position, a CT scan is performed. Using the images from the scan, an oncologist determines a treatment isocenter. When the oncologist determines the isocenter, a computer generates the coordinates for a laser projecting system. The lasers project beams onto the patient, indicating the three points of the coordinates. The center at which the three points intersect in the body defines the isocenter.

External marks are then placed on the patient's skin and used to align the patient for treatment. These external marks will indicate where the isocenter or center of treatment is within the patient's body. When the patient is aligned to these marks, prior to treatment, the isocenter will fall directly under the central axis of the radiation beam. Lining a patient up to these marks ensures that they are in the same position for treatment as they were at the time of simulation. The marks are then tattooed. These tattoos will be used during the course of treatment to reproduce how the patient was positioned during the CT scan.

There remains a need for improved devices and methods for marking isocenters on a patient's body.

SUMMARY

The present invention pertains to improved devices and methods for marking isocenters on a patient's body. An embodiment of the present invention may be found in an isocenter marker that includes a body, a biasing member, a plunger, a releasable lock and a lock actuator. The body includes a base and alignment indicia on the base. A handle on the base is configured for manipulating the body without interfering with laser illumination of the alignment indicia. The base includes a plunger support and an ink well receiving structure. The plunger includes a needle and a needle mount. The needle mount permits motion with respect to the plunger support between a retracted position at which the needle will be free from engagement with an ink well in the ink well receiving structure and a marking position at which the needle extends through an ink well in the ink well receiving structure. The biasing member biases the needle mount from the retracted position toward the marking position. The releasable lock is cooperable with the body to releasably hold the needle mount in the retracted position.

An embodiment of the present invention may be found in an isocenter marker alignment member. The isocenter marker alignment member includes alignment indicia structure, a handle on the alignment indicia structure, an ink well support on the alignment indicia structure and a needle actuator guide on the alignment indicia structure, the guide adapted to releasably position a needle actuator with respect to the alignment indicia structure and ink well support.

An embodiment of the present invention may be found in an isocenter needle actuator that includes a housing having a marking end and being configured to replaceably receive a needle having a tip and to support the needle for motion. The isocenter needle actuator includes a plunger in the housing for engaging the needle, the plunger movable between a cocked position at which the needle tip is located within the housing and a marking position at which the needle tip extends beyond the marking end of the housing. A first biasing member is included for driving the plunger from the cocked position to the marking position, as is a cocking actuator to move the plunger to the cocked position, a trigger for releasably retaining the plunger in the cocked position and a second biasing member for biasing the plunger to a retracted position between the cocked position and the marking position at which the needle tip is within the housing.

An embodiment of the present invention may be found in an isocenter marker that includes a base configured to removably receive ink wells, alignment indicia on the base, a handle on the base, a marking needle on the base and a needle actuator for causing the needle to move from a retracted position to a marking position.

An embodiment of the present invention may be found in an isocenter alignment marker that includes a base, an ink reservoir in the base, a porous needle guide sleeve in the ink reservoir and alignment indicia on the base.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 is a perspective view of a press version needle actuator, according to an exemplary embodiment of the present invention.

FIG. 5 is a cross-sectional view of the press version needle actuator of FIG. 4, according to an exemplary embodiment of the present invention.

FIG. 6 is a perspective view of an isocenter marker, according to an exemplary embodiment of the present invention.

FIG. 7 is an exploded perspective view of the isocenter marker of FIG. 6, according to an exemplary embodiment of the present invention.

FIG. 8 is a cross-sectional view of the isocenter marker of FIG. 6, according to an exemplary embodiment of the present invention.

FIG. 10 is an exploded perspective view of the isocenter marker of FIG. 9, according to an exemplary embodiment of the present invention.

FIG. 11 is a cross-sectional view of the isocenter marker of FIG. 9, according to an exemplary embodiment of the present invention.

FIG. 12 is a perspective view of an isocenter marker, according to an exemplary embodiment of the present invention.

FIG. 13 is a cross-sectional view of the isocenter marker of FIG. 12, according to an exemplary embodiment of the present invention.

FIG. 14 is a perspective view of an unassembled disposable cartridge usable with the isocenter marker of FIG. 12, according to an exemplary embodiment of the present invention.

FIG. 15 is a perspective view of the disposable cartridge of FIG. 14, shown assembled, according to an exemplary embodiment of the present invention.

FIG. 16 is a perspective view of an isocenter marker, according to an exemplary embodiment of the present invention.

FIG. 17 is a cross-sectional view of the isocenter marker of FIG. 16, according to an exemplary embodiment of the present invention.

FIG. 18 is a perspective view of a servo-operated isocenter marker alignment member, according to an exemplary embodiment of the present invention.

FIG. 19 is a perspective view of an internal portion of the servo-operated isocenter marker alignment member of FIG. 18, according to an exemplary embodiment of the present invention.

FIG. 20 is a perspective view of an internal portion of the servo-operated isocenter marker alignment member of FIG. 18, according to an exemplary embodiment of the present invention.

DETAILED DESCRIPTION

Figure 1:
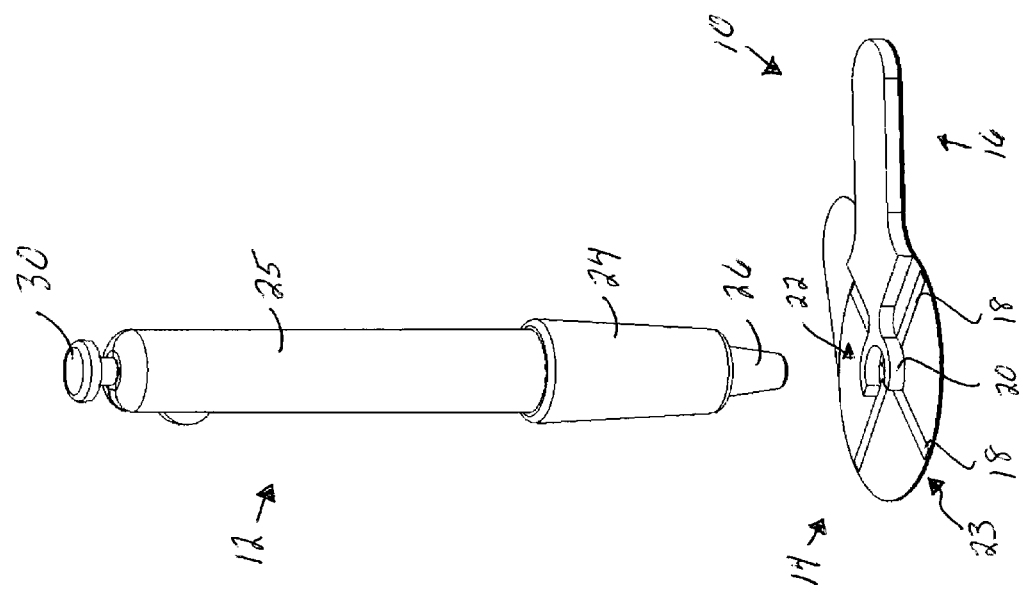
FIG. 1 is a perspective illustration of an isocenter marker alignment member and needle actuator configured for use therewith, according to an exemplary embodiment of the present invention.

FIG. 1 is a perspective illustration of an isocenter marker alignment member 10 and a needle actuator 12 configured for use with the isocenter marker alignment member 10. It will be appreciated that in some embodiments, the isocenter marker alignment member 10 may be aligned at a desired location on a patient's body and can then be releasably secured to the patient's skin at the desired location. The needle actuator 10 may subsequently be used to tattoo the patient at the location indicated by the isocenter marker alignment member 10.

The isocenter marker alignment member 10 includes a base 14 and a handle 16. In some embodiments, the handle 16 is an integral extension of the base 14 while in other embodiments the handle 16 may be separately formed and subsequently attached to the base 14. In some embodiments, the handle 16 is sized and configured to permit a user to easily grasp the handle 16 while not interfering with any projected laser beams used for alignment. The base 14 includes alignment indicia 18 that may be utilized for aligning the isocenter marker alignment member 10 with the aforementioned laser beams. In some embodiments, the alignment indicia 18 may include one or more of raised surface features or grooves extending into the base 14. In some embodiments, the alignment indicia may be white or otherwise permit easy viewing of the incident laser beams.

While not illustrated, the base 14 may include an adhesive portion on an underside (in the illustrated orientation) of the base 14 for releasably securing the isocenter marker alignment member 10 to a patient's skin. The adhesive portion, if present, may be covered by a removable release layer 23 that protects the adhesive portion until ready for use. In some embodiments, the base 14 is configured to guide the needle actuator 12. In the illustrated embodiment, the base 14 includes a needle actuator guide 20 that forms a raised, wall shaped to engage and guide the needle actuator 12. In some embodiments, an ink well support 22 is located at or near a center part of the needle actuator guide 20. The needle actuator guide 20 may be configured or adapted to releasably position the needle actuator 12 with respect to the alignment indicia 18 and the ink well support 22. While not illustrated, in some instances an ink well may be removably disposed within the ink well support 22.

In some embodiments, the needle actuator 12 is configured to accommodate disposable needles, thereby reducing the per patient cost. In some embodiments, the user may instead desire to treat the entire needle actuator 12 as being disposable, depending on economics and their preferences. The needle actuator 12 includes a main barrel 25 and a needle section 24 that is threadedly or otherwise removably attached to the main barrel 25. A tapered portion 26 that is configured to interact with the needle actuator guide 20 extends distally from the needle section 24. The main barrel 25, needle section 24 and tapered portion 26 may, in combination, be considered as forming a housing 28. An actuator cocking handle 30 extends proximally from the main barrel 25.

Figure 2:
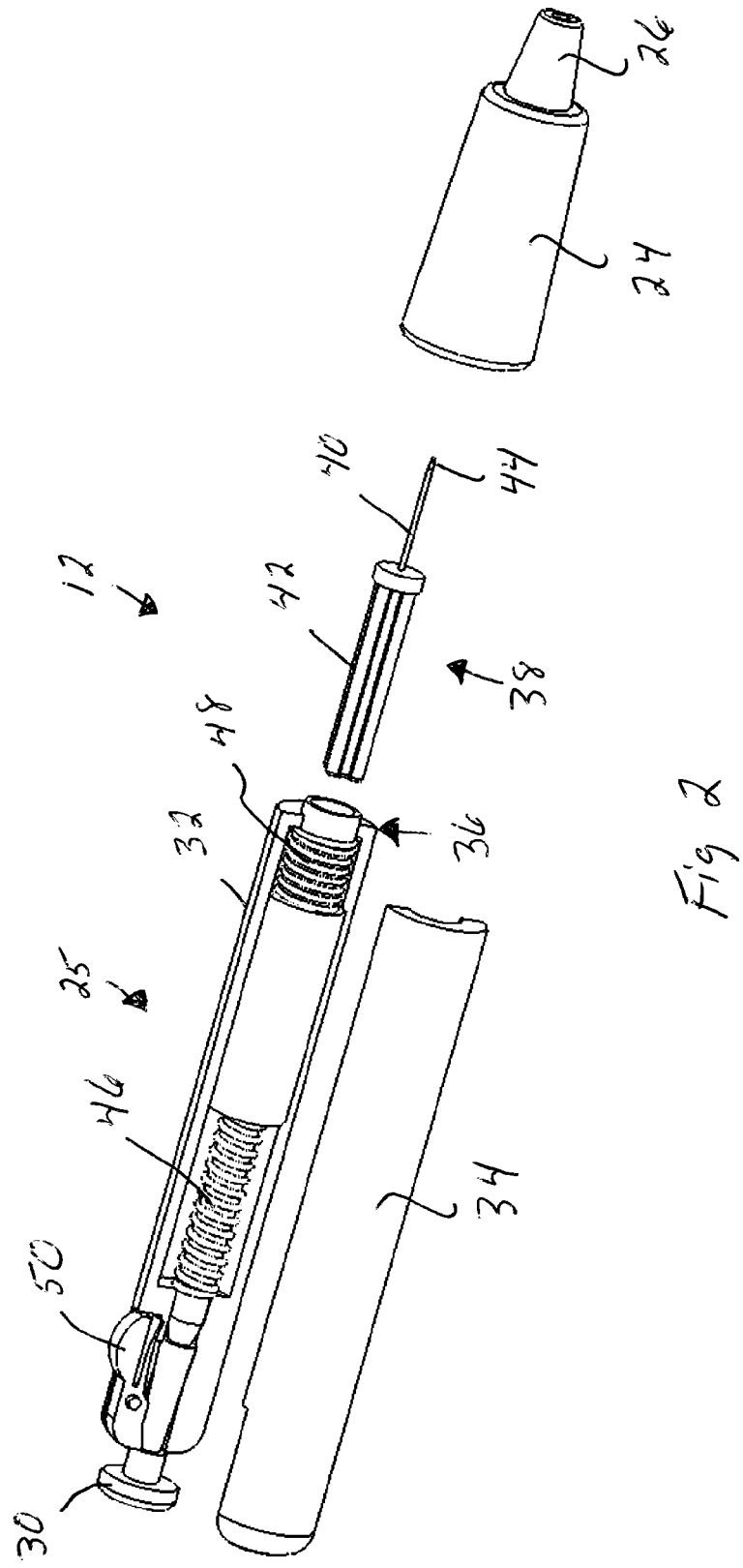
FIG. 2 is a partially exploded perspective view of the needle actuator of FIG. 1, according to an exemplary embodiment of the present invention.
Figure 3:
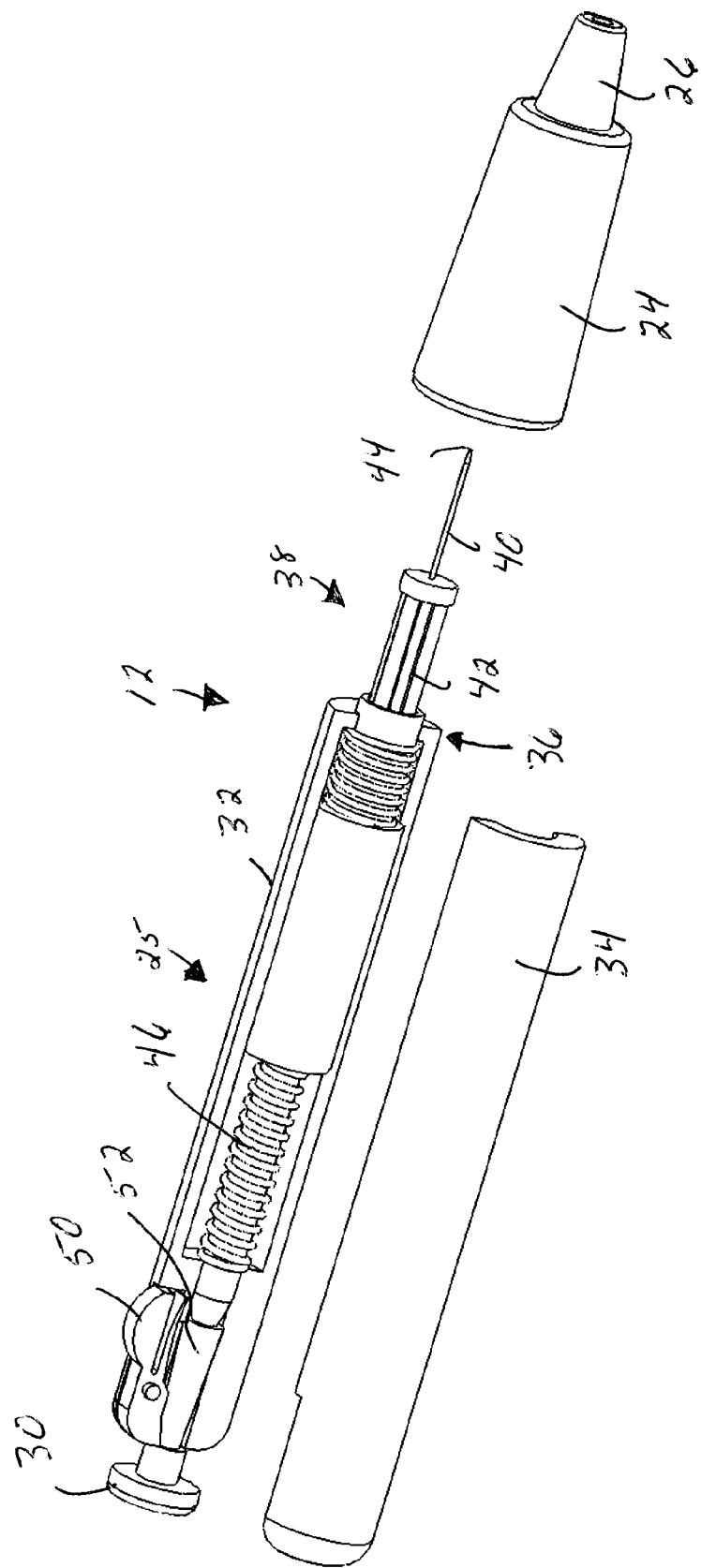
FIG. 3 is a partially exploded perspective view of the needle actuator of FIG. 1, according to an exemplary embodiment of the present invention.

FIGS. 2 and 3 are partially exploded perspective views of the needle actuator 12, illustrating that the main barrel 25 includes a first semi-cylindrical portion 32 and a second semi-cylindrical portion 34. The distal end 36 of the main barrel 25 is configured to accommodate a needle 38, as seen in FIG. 3. In some embodiments, as illustrated, the needle 38 includes a cylindrical needle 40 that is overmolded within a polymer portion 42. The needle 38 includes a distal end 44. The needle 38 is movable between a retracted position in which the distal end 44 of the needle 38 remains within the tapered portion 26 and a marking position in which the distal end 44 of the needle 38 extends distally from the tapered portion 26.

In some embodiments, the main barrel 25 is configured to accommodate a biasing mechanism that biases the needle 38 to its marking position. In some embodiments, the main barrel 25 is configured to accommodate a biasing mechanism that biases the needle 38 to its retracted position. As illustrated, a spring 46 and a spring 48 are disposed within the main barrel 25. A latch 50 interacts with a shaft 52. Once assembled with a needle 38 disposed within the needle section 24, the needle 38 is disposed in its retracted position. In some embodiments, the actuator handle 30 may be pulled backwards to cock against the spring 46, when the latch 50 latches onto the actuator handle 30. Pressing the latch 50 releases and causes the needle 38 to move distally relative to the tapered portion 26 such that the needle 38 extends distally of the tapered portion 26 a distance sufficient to permit the needle 38 to reach and penetrate at least partially into the patient's skin. If an ink well is disposed within the ink well support structure 22, the needle 38 will carry ink under the patient's skin, thereby tattooing the patient. The spring 48 returns the needle 38 to a position inside the main barrel 25.

FIGS. 4 and 5 illustrate an embodiment of a needle actuator 50 that may be used with an isocenter marker alignment member. The needle actuator 50 includes a housing 52, a tapered distal end 54 and an actuator 56. As can be seen in FIG. 5, the needle actuator 50 includes a needle 58 and an actuation shaft 60 that extends from the needle 58 to the actuator 56. The needle 58 is secured to the actuation shaft 60. In some embodiments, a proximal end of the actuation shaft 60 forms the actuator 56. A spring 62 is disposed within the needle actuator 50 and is configured to bias the actuation shaft 60, and hence the needle 58, into a retracted position. To use, the actuator 56 may be depressed to move the actuation shaft 60 against the spring 62, thereby extending the needle 58 distally out of the tapered distal end 54. In some embodiments, a safety plug 64 may include a raised portion 66 that is configured to interact with an aperture 68 that is formed within the tapered distal end 54 to hold the safety plug 64 in place until removal is desired.

FIG. 6 is a perspective view of an isocenter marker 70. In some embodiments, the isocenter marker 70 includes a base 72 and a handle 74 that extends from the base 72. The base 72 includes alignment indicia 76. In some embodiments, the handle 74 may be integrally molded with the base 72. A plunger assembly 78 extends upwardly from the base 72. It will be appreciated that in some embodiments, the plunger assembly 78 is sized and configured such that incident laser beams having an elevation angle of greater than about 45 degrees are not impeded or blocked by the plunger assembly 78.

In some embodiments, the plunger assembly 78 may be removably secured to the base 72 such that an ink well or other ink source may be replaced or otherwise disposed within the base 72. The plunger assembly 78 includes a plunger support 80 and an actuator 82. In some embodiments, the base 72 and the plunger assembly 78, in combination, include a tab and slot securement feature 84 that permits the plunger assembly 78 to be attached to the base 72 by positioning the plunger assembly 78 proximate the base 72 and rotating the plunger assembly 78 relative to the base 72 to secure the plunger assembly 78 in position.

FIG. 7 is an exploded view of the isocenter marker 70 while FIG. 8 is a cross-sectional view thereof, illustrating additional features of the isocenter marker 70. The isocenter marker 70 includes a plunger assembly 90 that includes a needle 92 extending downwardly (in the illustrated embodiment) from the actuator 82. A biasing mechanism such as a spring 94 is disposed between the plunger assembly 90 and the base 72. In some embodiments, the plunger assembly 90 includes an annular raised portion 104 that is sized to hold the actuator 82 within the plunger support 80. In some embodiments, as illustrated, the base 72 includes a raised portion 96 that anchors the spring 94. An ink source 98 may be secured underneath the base 72 using adhesively attached foil or other thin penetrable membrane material with a bubble ink reservoir contained between its layers. In some embodiments, the tab and slot securement feature 84 can be seen as including several tabs 100 that extend outwardly from the plunger support 80 and several corresponding slots 102 that are formed within the base 72 proximate the raised portion 96. In some embodiments, the tab and slot securement feature may be replaced by ultrasonic welding, adhesive, snap engagement features, or other means of assembling plunger support 80 to base 72.

In use, the spring 94 biases the needle 92 into a retracted position. The isocenter marker 70 may be positioned in a desired position on a patient without anchoring the isocenter marker 70. Once aligned using incident laser beams and the alignment indicia 76, a tattoo may be formed by depressing the actuator 82, thereby driving the needle 92 through an ink source and into the patient's skin. Once the actuator 82 is released, the spring 94 returns the needle 92 to its retracted position. The isocenter marker 70 may then be moved to another position on the patient, and the procedure may be repeated as desired to form additional alignment tattoos either with the same ink source 98 or upon replacement of ink source 98.

Figure 9:
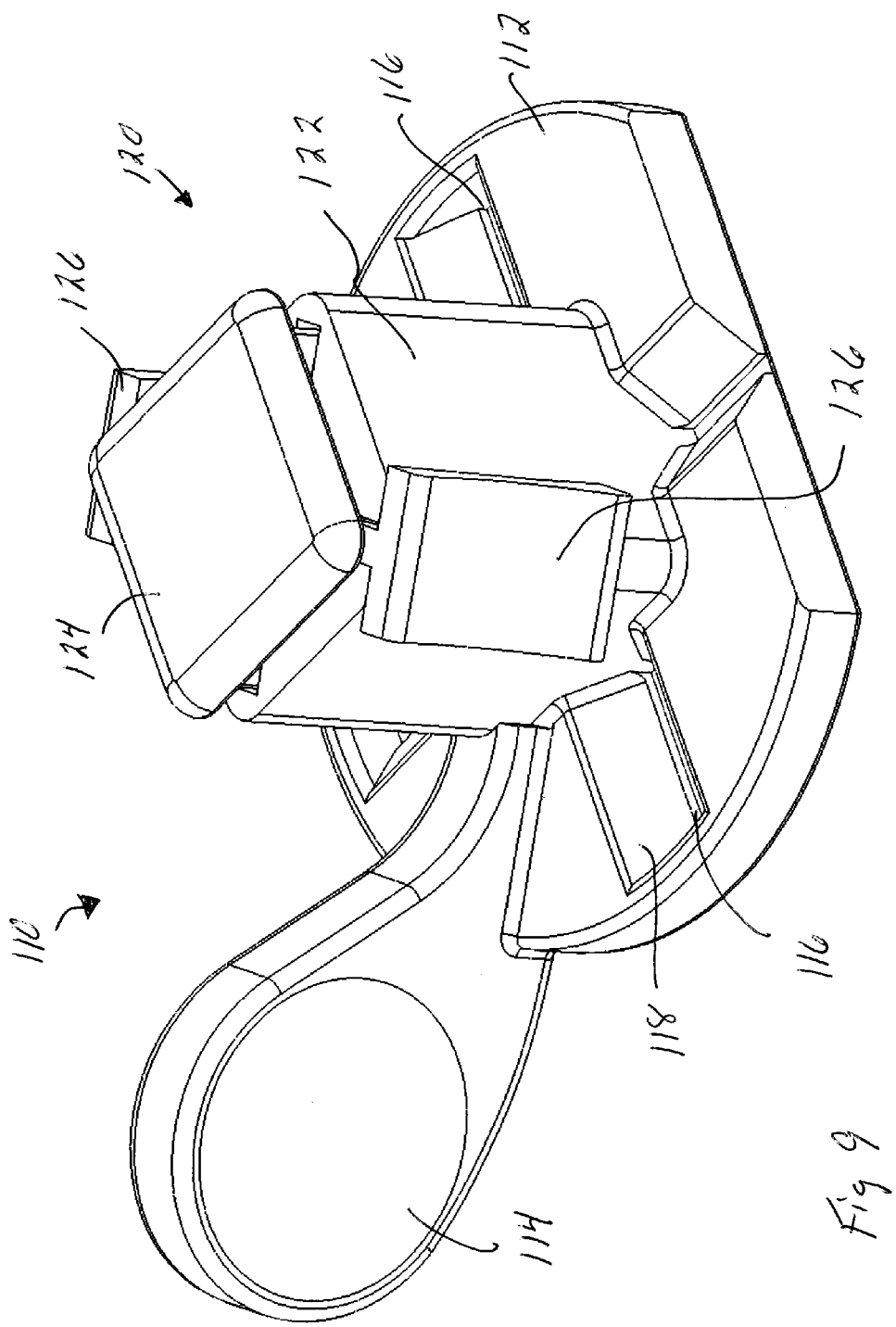
FIG. 9 is a perspective view of an isocenter marker, according to an exemplary embodiment of the present invention.

FIG. 9 is a perspective view of an isocenter marker 110. In some embodiments, the isocenter marker 110 includes a base 112 and a handle 114 that extends from the base 112. In some embodiments, the handle 114 is configured to enable the user to keep their hand far enough away from the base 112 to limit or prevent laser shadows. The base 112 includes alignment indicia 116. In some embodiments, the alignment indicia 116 form or otherwise include tapered grooves 118 formed within the base 112. In some embodiments, the handle 114 may be integrally molded with the base 112. A plunger assembly 120 extends upwardly from the base 112. The plunger assembly 120 includes a plunger support 122, an actuator 124 and a release actuator 126. In some embodiments, the actuator 124 and the release actuator 126 are integrally molded. In some embodiments, as will be described with respect to FIGS. 10 and 11, the actuator 124 may not be deployed unless the user also engages the safety mechanism 126.

FIG. 10 is an exploded perspective view of the isocenter marker 110 while FIG. 11 is a cross-sectional view thereof, illustrating additional features of the isocenter marker 110. The plunger support 122 includes a first groove 128 that is configured to accommodate a biasing mechanism 130 that is affixed or otherwise secured to the actuator 124 as well as a second groove 132 that is configured to accommodate an alignment tab 134. The actuator 124 includes a central structure 136 to which the alignment tab 134 is affixed or otherwise secured. A needle 138 extends downward (in the illustrated embodiment) from the central structure 136.

The second groove 132 has a bottom surface 140 that is configured to interact with a lower surface 142 of the release actuator 126. It will be appreciated, particularly with respect to FIG. 11, that the bottom surface 140 of the second groove 132 prevents further downward movement of the actuator 124. However, by pressing the release actuator 126 inwardly, the lower surface 142 of the release actuator 126 moves inwardly and is no longer blocked by the bottom surface 140 of the second groove 132. Instead, the release actuator 126 includes a channel 144 that accommodates the plunger support 122 and permits limited downward travel of the actuator 124. As a result, the needle 138 is permitted to extend downwardly a distance that accommodates a desired depth of penetration into the patient's skin.

The isocenter marker 110 includes a label 150 that may be affixed to a lower surface of the base 112. The label 150 includes an ink reservoir 152 such that when the needle 138 moves downward, the needle 138 penetrates the ink reservoir 152 and carries a small amount of ink into the patient's skin to create a tattoo. In some embodiments, the label 150 includes areas of increased or decreased surface reflectivity 154 that align with the alignment indicia 116 formed in the base 112, particularly in instances when the alignment indicia 116 include apertures extending through the base 112, such that increased contrast with base 112 improves visibility of laser alignment precision.

FIG. 12 is a perspective view of an isocenter marker 160. In some embodiments, the isocenter marker 160 includes a disposable cartridge 162 that can be placed into an actuator assembly 164. As can be seen in FIGS. 14 and 15, the disposable cartridge 162 includes the components that need to be changed for each patient, i.e., a needle 166 and an ink reservoir 168. The disposable cartridge 162 may be molded as a unitary structure 170 including a needle arm 171, a needle 166 may be attached and the unitary structure 170 may be folded along living hinges to form the assembled disposable cartridge 162. An adhesive label that bears the ink reservoir 168 may be applied to the disposable cartridge 162 to properly locate the ink reservoir 168 as well as to hold together the folded unitary structure 170. Although not illustrated, the base 170 may include alignment indicia as discussed herein with respect to other embodiments.

The actuator assembly 164 includes a cocking mechanism 174. The cocking mechanism 174 includes a handle 176, a shaft-shaped hammer 178 bearing a spring 180, a cocking handle 172, and a latch mechanism 182. In use, once a disposable cartridge 162 has been disposed within the isocenter marker 160, cocking the handle 172 pulls back the hammer 178, compressing the spring 180. Releasing the latch mechanism 182 causes, by virtue of the spring force of the spring 180, the hammer 178 to move forward striking a rear portion of the needle arm 171, causing the needle arm 171 to swing down. As a result, the needle 166 penetrates the ink reservoir 168. After use, the disposable cartridge 162 may be disposed and the actuator assembly 164 may be used again for another patient.

FIG. 16 is a perspective view of an isocenter marker 190 while FIG. 17 is a cross-sectional view thereof. The isocenter marker 190 includes a handle assembly 192 and a base 194. The handle assembly 192 is configured to accommodate a disposable cartridge 196 that includes a needle 198 and an ink reservoir 200. In some embodiments, the base 194 is configured to electronically detect the alignment lasers, and thus may include one or more sensors 202 disposed within alignment indicia 204. An on/off switch 206 may be used to turn the electronics (not illustrated) on and off, and several indicator lights 208 inform the user whether alignment has been achieved. In some embodiments, the indicator lights 208 may be colored LEDs.

The handle assembly 192 includes an actuator button 210. A shaft 212 is held in a rearward position against the force of a biasing spring 214. When the actuator button 210 is released, the shaft 212 moves towards the disposable cartridge 196. The shaft 212 pushes on an actuator bar 216 that moves along an incline on a needle spring arm 218, thereby causing the needle spring arm 218 to move downwardly (in the illustrated orientation), pushing needle 198 to penetrate the ink reservoir 200 and tattoo the patient. After full actuation, the actuator bar 216 becomes trapped beyond the automatically retracting needle spring arm 218 and needle 198, making the disposable cartridge save against an accidental second needle exposure. After use, the disposable cartridge 196 may be removed and the isocenter marker 190 is ready for use with another patient.

FIG. 18 is a perspective view of an isocenter marker alignment member 250 while FIGS. 19 and 20 illustrate internal components thereof. In some embodiments, the isocenter marker alignment member 250 is servo-operated, meaning that it electronically detects the incident aligning laser beams and adjust itself accordingly. The isocenter marker alignment member 250 includes an alignment aperture 252 that is secured to orthogonally arranged sliding members 254 and 256. The isocenter marker alignment member 250 includes motor driven assemblies 258 and 260 that cause motion of the sliding members 254 and 256, respectively. Alignment slots 262 permit incident laser light to pass through and strike sensors 264. The sensors 264 are configured to detect the laser light and provide signals to integrated circuit assemblies not shown. Sensor 266 and 268 are mounted at an elevation proud of the 4 sensors 264 such that the angle of incidence of the laser beams may be inferred and the proper parallax adjustment to the position detected by sensors 264 may be included in the positioning calculation, after which the integrated circuit provides movement instructions to the motor driven assemblies 258 and 260 in order to align the device. Once aligned, the alignment aperture 252 is used for positioning any tattoo marker device.

In some embodiments, as illustrated, the isocenter marker alignment member 250 includes an adhesive layer that permits adhering the device to the patient in the general area of the laser markers to which it will self align by means of the servos. The adhesive layer is visible in FIGS. 18-20 only where tab 270 of the adhesive layer protrudes from under the device. Release liner tab 272 is visible beneath tab 270. After device use, the adhesive layer 270 and the release liner 272 are replaced for subsequent uses.

Figure 21:
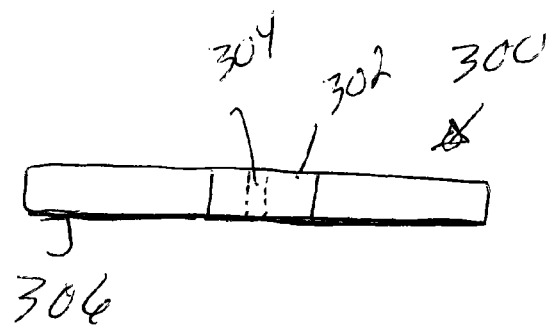
FIG. 21 is a schematic view of an ink disk, according to an exemplary embodiment of the present invention.
Figure 22:
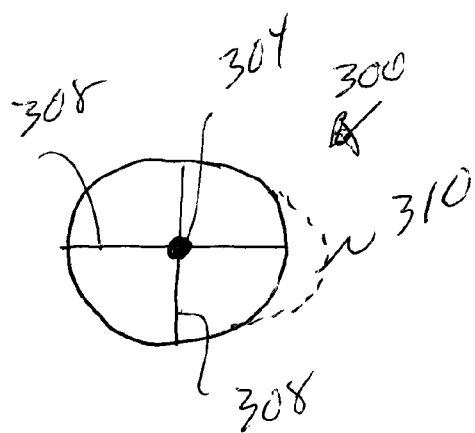
FIG. 22 is a top view of the ink disk of FIG. 21, according to an exemplary embodiment of the present invention.

FIG. 21 is a schematic view of an ink disk 300 while FIG. 22 is a top view thereof. The ink disk 300 includes an ink reservoir 302 and a porous needle guide sleeve 304. The guide sleeve 304 is sufficiently porous to permit ink to pass from the ink reservoir 302 into the guide sleeve 304. In some embodiments, the ink disk 300 may include an adhesive backing 306 that may be used to releasably secure the ink disk 300 to a patient. While not illustrated, in some cases the ink disk 300 may include a release liner that protects the adhesive backing 306 until the ink disk 300 is ready for use. The ink disk 300 includes alignment indicia 308 and in some embodiments may include a handle tab 310.

Figure 23:
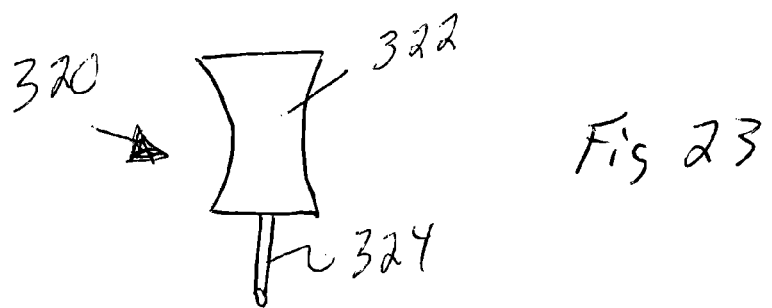
FIG. 23 is a schematic view of a needle assembly, according to an exemplary embodiment of the present invention.

FIG. 23 is a schematic view of a needle assembly 320 that may be used in combination with the ink disk 300. The needle assembly 320 includes an overmolded polymer member 322 that is configured to permit the user to easily grasp the needle assembly 320. The needle assembly 320 also includes a needle 324 that is sized and configured to penetrate a patient's skin to a desired depth.

Figure 24:
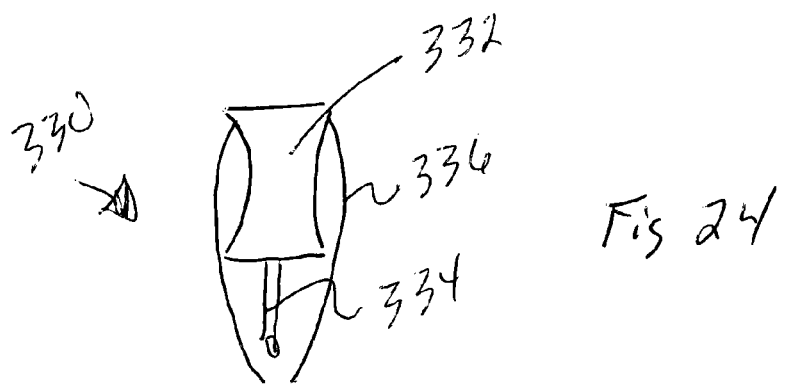
FIG. 24 is a schematic view of a needle assembly including a safety guard, showing the safety guard in an extended position according to an exemplary embodiment of the present invention.
Figure 25:
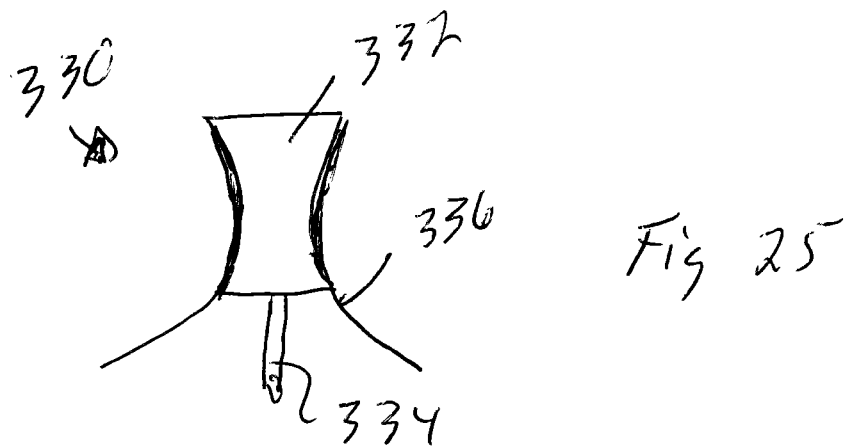
FIG. 25 is a schematic view of the needle assembly and safety guard of FIG. 24, showing the safety guard in a retracted position according to an exemplary embodiment of the present invention.

FIGS. 24 and 25 are schematic views of a needle assembly 330 that may be used in combination with the ink disk 300. The needle assembly 330 includes an overmolded polymer member 332 that is configured to permit the user to easily grasp the needle assembly 330. The needle assembly 330 also includes a needle 334 that is sized and configured to penetrate a patient's skin to a desired depth. The needle assembly 330 also includes a safety guard 336. In FIG. 24, the safety guard 336 is shown in an extended position in which the needle 334 is at least partially covered to limit or prevent accidental sticks. In FIG. 25, the safety guard 336 is shown in a retracted position in which the needle 334 is exposed and is ready for use. In some embodiments, the safety guard 336 may be moved into the retracted position by squeezing an upper portion of the safety guard 336. In some embodiments, the safety guard 336 is self-biased to remain in the extended position, and only remains in the retracted position while a user applies pressure to the safety guard 336.

Figure 26:
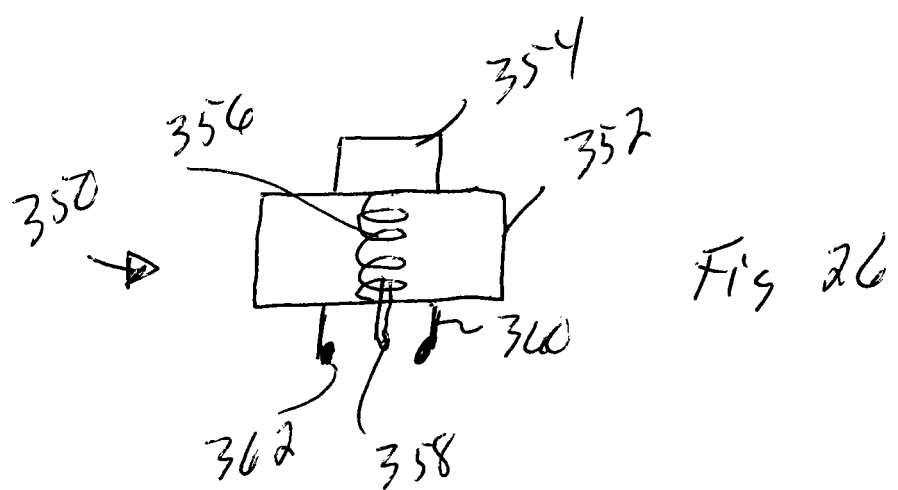
FIG. 26 is a schematic view of a pushbutton needle assembly, according to an exemplary embodiment of the present invention.
Figure 27:
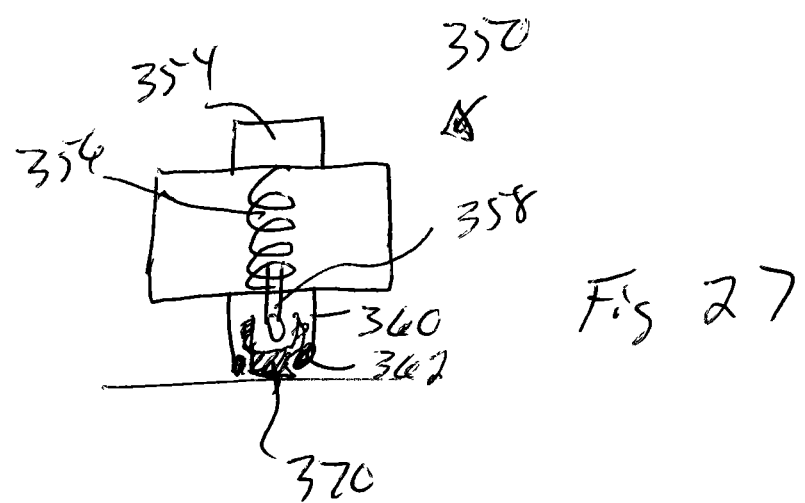
FIG. 27 is a schematic view of the pushbutton needle assembly of FIG. 26, in combination with an ink well, according to an exemplary embodiment of the present invention.

FIG. 26 is a schematic view of a push button needle assembly 350. The push button needle assembly 350 includes a housing 352 and a button 354. A spring 356 extends between the button 354 and a needle 358. It will be appreciated that depressing the button 354 will compress the spring 356 and cause the needle 358 to move downward (in the illustrated orientation). The push button needle assembly 350 includes a needle guard 360. In some embodiments, the needle guard 360 includes locking nubs 362 that are configured to releasably engage with the profile of an ink reservoir, as shown in FIG. 27. In FIG. 27, it can be seen that an ink reservoir 370 includes a side profile that complements the locking nubs 362 and thus help to locate the push button needle assembly 350 relative to the ink reservoir 370.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An isocenter marker, comprising:
   a body including:
      a base;
      an ink well receiving structure;
      alignment indicia on the base at circumferentially-spaced locations with respect to the ink well receiving structure, wherein the alignment indicia are configured for alignment with external alignment sources to facilitate alignment of the base over an isocenter;
      a handle extending from the base at a location between a first and a second of the alignment indicia for manipulating the body without substantial interference with alignment of the alignment indicia with external alignment sources;
      a plunger support on the base;
   a biasing member;
   a plunger including:
      a needle mounted for motion with respect to the plunger support between a retracted position at which the needle will be free from engagement with an ink well in the ink well receiving structure and a marking position at which the needle extends through an ink well in the ink well receiving structure, wherein the biasing member biases the needle from the retracted position toward the marking position;
      a releasable lock cooperable with the body to releasably hold the needle in the retracted position; and
      a lock actuator, wherein upon actuation of the lock actuator when the releasable lock is holding the needle in the retracted position, the biasing member causes the needle to move from the retracted position to the marking position.

2. The isocenter marker of claim 1 wherein the lock actuator is coupled to the lock and includes a biasing member biasing the lock to a locked position with respect to the body.

3. The isocenter marker of claim 2 wherein:
   the body is a first one-piece molded polymer member; and
   the biasing member and plunger are elements of a second one-piece molded polymer member.

4. The isocenter marker of claim 3 and further including an ink well in the ink well receiving structure.

5. The isocenter marker of claim 1 wherein:
   the first and second alignment indicia are radially spaced from the ink well receiving structure; and
   the handle includes at least portions at locations radially spaced from the ink well receiving structure by a distance greater than distances that the first and second alignment indicia are located from the ink well receiving structure.

6. The isocenter marker of claim 5 wherein:
   the base has a generally planar major surface, and wherein the alignment indicia are on the planar major surface; and
   the handle extends to a height with respect to the planar major surface that is greater than a height of the alignment indicia with respect to the planar major surface.

7. An isocenter marker, comprising:
   a base, the base configured to removably receive ink wells;
   a marking needle on the base;
   alignment indicia on the base at circumferentially-spaced locations with respect to the marking needle, wherein the alignment indicia are configured for alignment with external alignment sources to facilitate alignment of the base over the isocenter;
   a handle extending from the base at a location between a first and a second of the alignment indicia, for manipulating the base without substantial interference with alignment of the alignment indicia with external alignment sources;
   a biasing member to bias the marking needle from a retracted position at which the needle will be free from engagement with an ink well toward a marking position at which the needle extends through an ink well; and
   a needle actuator, wherein the needle actuator causes the biasing member to move the needle from the retracted position to the marking position through an ink well when actuated by a user.

8. The isocenter marker of claim 7 and further including an ink well removably mounted to the base.

9. The isocenter marker of claim 7 wherein the needle actuator includes:
   a housing;
   an actuator on the housing for moving the needle from the retracted position to the marking position; and
   the biasing member is in the housing and biases the needle and actuator to the retracted position.

10. The isocenter marker of claim 7 wherein:
    the first and second alignment indicia are radially spaced from the marking needle; and
    the handle includes at least portions at locations radially spaced from the marking needle by a distance greater than distances that the first and second alignment indicia are located from the marking needle.

11. The isocenter marker of claim 10 wherein:
    the base has a generally planar major surface, and wherein the alignment indicia are on the planar major surface; and
    the handle extends to a height with respect to the planar major surface that is greater than a height of the alignment indicia with respect to the planar major surface.

12. A method for using the isocenter marker of claim 7, including:
    placing a first ink well on the base;
    positioning the marker with the first ink well on a patient, including grasping the handle and aligning the alignment indicia with external alignment sources;

actuating the needle actuator to place a first isocenter mark on a patient using the first ink well;

removing the first ink well from the base;

placing a second ink well on the base;

positioning the marker with the second ink well on the patient, including grasping the handle and aligning the alignment indicia with the external alignment sources;

actuating the needle actuator to place a second isocenter mark on the patient using the second ink well;

optionally repeating the steps of removing the ink well, placing an ink well positioning the marker and actuating the needle actuator to place third and/or additional isocenter marks on the patient; and disposing the marker after use on the patient.

13. An isocenter alignment marker, comprising:

a base;

an ink reservoir in the base;

a marking needle;

a porous needle guide sleeve in the ink reservoir; and alignment indicia on the base at circumferentially-spaced locations with respect to the marking needle; and a handle on the base at a location between a first and a second of the alignment indicia.

14. The alignment marker of claim 13 wherein the marking needle comprises:

a finger hold having a concave finger-engaging surface; and a needle extending from an end of the finger hold.

15. The alignment marker of claim 14 and further including a retractable safety guard around the needle.

16. The alignment marker of claim 15 wherein the safety guard includes:

a guard member around the needle movable from a guard position to a retracted position; and an actuator member coupled to the guard member and located adjacent to the finger hold, wherein the actuator member is configured to be engaged and pressed onto the finger-engaging surface of the finger hold when a user grabs the finger hold, and to move the guard member to the retracted position when pressed onto the finger hold.

17. The alignment marker of claim 16 wherein the guard member is biased to the guard position and returns to the guard position when the finger hold is released.

18. The alignment marker of claim 13 wherein the marking needle comprises:

a finger hold; and a needle extending from an end of the finger hold.

19. The alignment marker of claim 18 and further including a retractable safety guard around the needle, the safety guard including:

a guard member around the needle movable from a guard position to a retracted position; and an actuator member coupled to the guard member and located adjacent to the finger hold, wherein the actuator member is configured to be engaged and pressed onto the finger hold when a user grabs the finger hold, and to move the guard member to the retracted position when pressed onto the finger hold.

20. The alignment marker of claim 19 wherein the guard member is biased to the guard position and returns to the guard position when the finger hold is released.

21. The isocenter marker of claim 13 wherein:

the first and second alignment indicia are radially spaced from the marking needle; and the handle includes at least portions at locations radially spaced from the marking needle by a distance greater than distances that the first and second alignment indicia are located from the marking needle.

22. The isocenter marker of claim 21 wherein:

the base has a generally planar major surface, and wherein the alignment indicia are on the planar major surface; and the handle extends to a height with respect to the planar major surface that is greater than a height of the alignment indicia with respect to the planar major surface.

* * * * *